United States Patent [19]
Rada

[11] Patent Number: 6,094,923
[45] Date of Patent: Aug. 1, 2000

[54] TISSUE FREEZING APPARATUS

[76] Inventor: David C. Rada, 248 Lake Shore West, Lake Quivira, Kans. 66106

[21] Appl. No.: 09/163,641

[22] Filed: Sep. 30, 1998

Related U.S. Application Data

[63] Continuation-in-part of application No. 08/855,857, May 12, 1997, Pat. No. 5,829,256.

[51] Int. Cl.$^7$ .............................. F25B 19/00; F25D 25/00
[52] U.S. Cl. ................................... 62/51.1; 62/62; 62/381
[58] Field of Search .............................. 62/51.1, 62, 381, 62/499

[56] References Cited

U.S. PATENT DOCUMENTS

| | | | |
|---|---|---|---|
| 3,209,821 | 10/1965 | Zeytoonian | 165/185 |
| 3,218,896 | 11/1965 | McCormick . | |
| 3,296,821 | 1/1967 | Malinin . | |
| 3,520,055 | 7/1970 | Jannett . | |
| 3,598,066 | 8/1971 | Gerber . | |
| 3,654,019 | 4/1972 | Cusik . | |
| 3,667,330 | 6/1972 | Kobernick . | |
| 3,737,335 | 6/1973 | Feinberg . | |
| 3,742,802 | 7/1973 | Maerz . | |
| 3,744,262 | 7/1973 | Bose . | |
| 3,765,289 | 10/1973 | Gerber . | |
| 3,803,958 | 4/1974 | Fernandez-Moran . | |
| 3,832,923 | 9/1974 | Lassmann et al. . | |
| 3,948,061 | 4/1976 | Kidwell . | |
| 4,012,475 | 3/1977 | Kindel . | |
| 4,060,440 | 11/1977 | Behme . | |
| 4,190,472 | 2/1980 | Slonicki . | |
| 4,532,838 | 8/1985 | Söderkvist . | |
| 4,543,862 | 10/1985 | Levene . | |
| 4,545,831 | 10/1985 | Ornstein . | |
| 4,553,406 | 11/1985 | Richelli et al. . | |
| 4,695,339 | 9/1987 | Rada . | |
| 4,751,828 | 6/1988 | Coulter et al. . | |
| 4,752,347 | 6/1988 | Rada . | |
| 5,168,726 | 12/1992 | York . | |
| 5,364,756 | 11/1994 | Livesey et al. | 435/2 |
| 5,780,295 | 7/1998 | Livesey et al. | 435/307.1 |

OTHER PUBLICATIONS

Evaluation of a Method for Controlled Tissue Embedding for Histologic Evaluation of Tumor Margins; Daniel E. Gormley, M.D.; *The American Journal of Dermatopathology*; 9(4); 308–315, 1987.

Chemosurgical Reports: Frozen–Section Processing with the Miami Special; C. William Hanke, M.D. et al; *J. Dermatol. Surg. Oncol.* 9:4 Apr. 1983.

Mohs Surgery; Neil A. Swanson, M.D.; *Arch Dermatol*—vol. 119, Sep. 1983.

A New Method for Preparing Tissue Blocks for Cryostat Sectioning; Vernon H. Carter, M.D.; *J. Dermatol. Surg. Oncol.* 11:7 Jul. 1985.

How to Prepare Tissue Blocks; Justo Concepcion; (published as Letter to the Editor), *J. Dermatol. Surg. Oncol.* 12:2 Feb. 1986.

Technical Procedures for Mohs Fresh Surgery; Ana Maria Picoto Antonio Picoto, M.D.; *J. Dermatol. Surg. Oncol.* 12:2 Feb. 1986.

*Primary Examiner*—William Doerrler
*Attorney, Agent, or Firm*—John C. McMahon

[57] ABSTRACT

An apparatus for cryogenically freezing tissue specimens includes a linear motion platform and a pair of rotary motion platforms. The rotary motion platforms can be used alternatively with respect to the linear motion platform and a mechanism is provided to automatically trigger the linear motion platform for movement and to reset the linear motion platform when the rotary motion platforms are placed in covering relationship with or removed from covering relationship with respect to the linear motion platform. Cryogenic fluids are supplied to tissue receiving cryogenic discs on the various platforms through flexible plastic tubing. The tubing that supplies cryogenic fluid to the rotary motion platforms is constructed so as to form a series of loose loops in conjunction with tails that are mounted over a central rod to allow movement at cryogenic temperatures. A rapid frost mechanism nebulizes water and delivers a fine spray across the cryogenic discs associated with the linear motion platform to form a layer of frost on prechilled discs. Specimen receiving plates contact the frost layer to effect accelerated, uniform heat transfer.

13 Claims, 5 Drawing Sheets

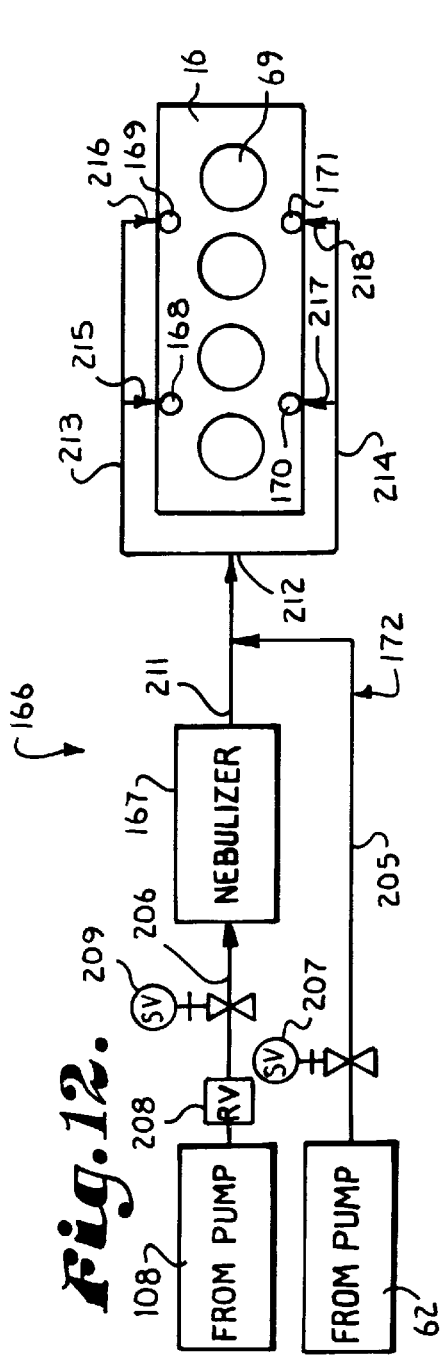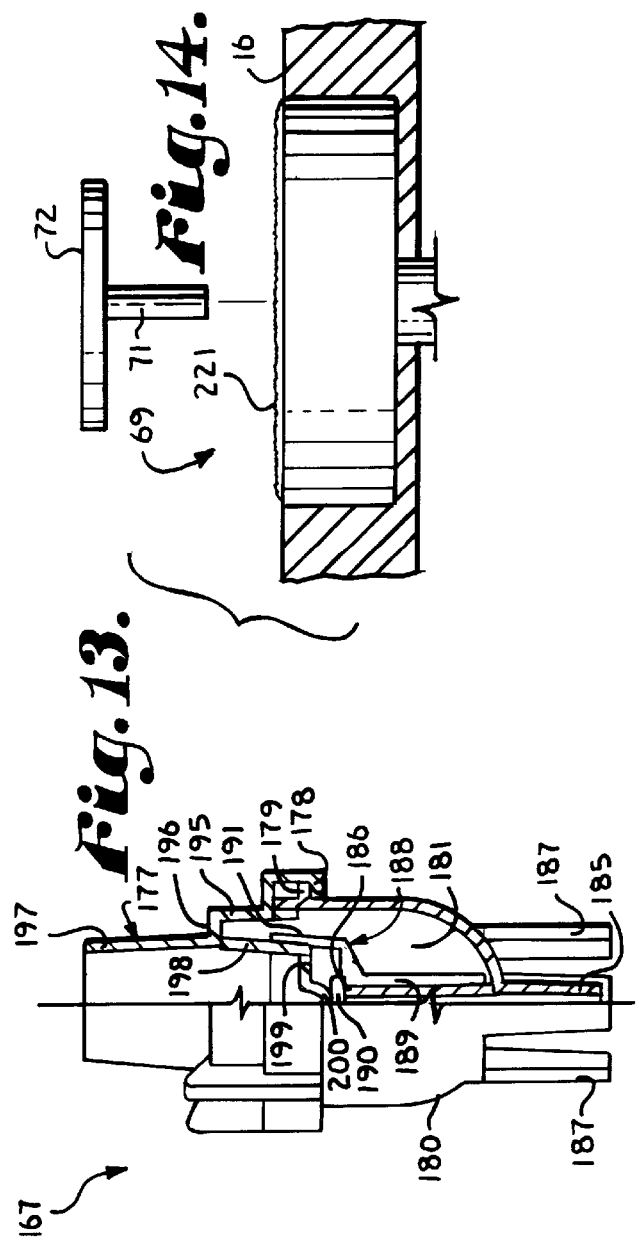

TISSUE FREEZING APPARATUS

CROSS REFERENCE TO RELATED APPLICATIONS

This application is a continuation-in-part of U.S. patent application Ser. No. 08/855,857 filed May 12, 1997, now U.S. Pat. No. 5,829,256 and entitled SPECIMEN FREEZING APPARATUS.

BACKGROUND OF THE INVENTION

The present application is directed to an apparatus for rapidly freezing tissue specimens, especially potential human cancer tissue at cryogenic temperatures, especially with liquid nitrogen.

Many types of medical procedures surgically remove tissue to test the tissue so as to determine whether or not malignant growth is present. For example, various suspected skin cancers or neoplasms are tested by excising the suspected growth area and then microscopically checking the tissue to determine whether or not cancer is present.

It is also important during such surgical procedures to ensure that all cancerous growth associated with a tumor has been removed. For this purpose the exterior or margins of the excised tissue are studied microscopically to ensure that they are clear of cancerous tissue. The study of the margins requires that the tissue first be hard frozen and then sliced into extremely thin sections. The purpose of the apparatus of the present invention is to prepare specimens for slicing. In particular, the apparatus of the present invention is designed to freeze tissue specimens so that the frozen tissue will have sufficient rigidity in order to be able to be easily sliced and microscopically studied.

The present apparatus represents additional improvements to four previous devices developed by the inventor of the subject of the present application. Applicant's previous patents have included U.S. Pat. Nos. 4,695,339; 4,752,347; 5,628,197 and 5,829,256 which have described various devices and methods for preparing specimens as required for slicing. Certain aspects and procedures which are common to the present application and to one or more of applicant's prior applications and certain of those features which are not new to the present application are not redescribed herein. Consequently, these four previous patents are incorporated herein by reference and should be referred to with reference to further describing certain elements or methods of use of the present invention.

The subject matter of the present application is directed to features which are designed to improve and increase the efficiency and ease of operation of the tissue freezing apparatus and to expand the range of tissue types and size of samples for which it may be employed. In particular, perhaps the most important concern with respect to such a specimen freezing apparatus is that it is always important for the specimens to be frozen as quickly as possible.

There are a number of reasons for expediency, one of the most important of which is that the surgery on the patient must effectively continue until the doctor is convinced that there is no further sign of cancer in the tumor margins. That is, the doctor will initially remove a tissue specimen from the patient that the doctor believes will probably be large enough to contain all of the cancerous tumor.

However, if microscopic study of the margins of the removed tissue demonstrate that cancer has grown outside of the excised tissue, then the doctor must return to the patient and remove a subsequent additional tissue specimen. This subsequent specimen is then tested in the same manner as the first and this process is continued until the specimen proves to be clear of cancerous tissue.

Furthermore, the doctor's time associated with the process is expensive and it is desirable to limit such time. Perhaps one of the more important aspects of the process is that it has been found that relatively fast freezing of the tissue which is referred to as snap freezing produces a much better histologically clean specimen, as compared to slow freezing. The snap freezing reduces crystal formation and provides an overall better specimen to study.

Because of its speed, snap freezing provides rate-controlled freezing in which the speed of heat transfer away from the specimen is more uniform and predictable from one specimen to another. Such high speed heat transfer permits handling of larger individual specimens of all tissues, as well as specimens of tissues which must be sectioned at lower temperatures, such as tissues having a high fat content. Previously, in order to achieve satisfactory microscopic morphology, only smaller specimens of certain tissues such as liver, kidney, fatty tissues and lymph nodes could be handled with conventional slow freezing methods. Consequently, for all these reasons and others, it is highly important to freeze the tissue specimen as quickly as possible.

The apparatus of the present application is specifically designed to improve the quick freezing of the specimen while also providing a number of additional advantages to the process.

One of the problems associated with the prior devices has been that there has been a limitation as to how quickly a physician utilizing the device may process multiple samples. Therefore, it is desirable to be able to process and get ready one set of specimens while another set is in the freezing process. In order to accomplish this the apparatus must include multiple receiving plates which function in cooperation with each other to allow use of the single apparatus with multiple plates. This produces a number of problems since one of the main concerns in processing of the specimen is that the specimen not be rolled sideways on itself during processing steps. Therefore, it is extremely desirable for the opposed plates of the freezing apparatus, once in facing relationship to one another, to move toward each other in a linear fashion as opposed to sliding angularly into each other. An apparatus for accomplishing this process was developed in U.S. Pat. No. 5,628,197 noted above, but this apparatus only functioned in conjunction with a single linear moving plate and a single rotary moving plate. Therefore, it is desirable to develop an apparatus utilizing a single linear moving plate but being able to cooperatively utilize multiple rotary plates that allow preparation actively of some specimens while other specimens are freezing.

The extreme cold associated with cryogenic fluids, especially liquid nitrogen, utilized in conjunction with the apparatus for freezing specimens, produces a number of problems. Obviously, the operator of the apparatus must be quite careful and avoid touching much of the device. Therefore, the operator must take great care in working with the device.

Not only do the cryogenic temperatures present problems to the operator, but also to the apparatus. One of these problems is respect to delivery of the liquid nitrogen to cryogenic discs of the rotary motion platforms. That is, the rotary motion plates of the present apparatus rotate around an axis of approximately 180° and in such rotation the cryogenic fluid supply lines to the disc are likewise rotated. This would not be a problem at room temperature, but the severe cold presents a substantial problem at cryogenic temperatures, since almost all materials which are flexible enough to be rotated at room temperature become fairly rigid at cryogenic temperatures. Consequently, it is difficult to design plastic tubing or the like which can be utilized for this purpose. Rotary quartz couplings have been used in previous embodiments. The quartz couplings function, but tend to be expensive and it is desirable to produce a structure constructed of plastic tubing which will function for this purpose.

It has previously been recognized that quick freezing is an important aspect of the present invention both with respect to speed and quality. However, with respect to speed, it may be as important to be able to heat up the cryodisc to get each of the cryodiscs ready for subsequent specimens.

It is also important for the tissue receiving plates located on the cryodiscs of the linear motion platform to be spaced away from the remainder of the cryodiscs prior to the freezing stage so that the specimen will be more likely to adhere to the plate when it is placed thereon. Consequently, it is desirable to incorporate elements into the apparatus to improve the ability to heat the cryodiscs to near room temperature subsequent to use in freezing a specimen so as to place it in condition for receiving new specimens and to help keep the plate from being chilled prematurely to the placement of the specimen thereon.

It is also desirable within such structures to independently operate at least some of the cryodiscs with respect to others associated with a single platform. That is, for example, in an apparatus having four sets of cryodiscs on each of the linear motion plates and the outer rotary motion plates, it may be desirable to be able to use just two or perhaps only one of those discs depending upon the number of specimens being tested. Consequently, it is desirable to provide the physician with the ability to select all of the discs for use at a time or, when the number of specimens to be tested is less than the number of discs available, to be able to select and quickly freeze a smaller number of the discs.

Another problem associated with prior devices was the difficulty of achieving predictable rate-controlled snap freezing for tissue specimens of all types and sizes, with repeatable results. Certain types of tissue freeze more quickly, whereas other tissues freeze more slowly, with resulting greater incidence of cellular artifacts. Prior devices were more effective at snap freezing smaller tissue specimens. In prior devices the high speed heat transfer required for snap freezing was more difficult to achieve consistently with specimens of larger size. Prior devices were also less effective at snap freezing specimens of tissues having high fat content, which must be sectioned at temperatures as low as about –40° C. to –50° C. Thus, it is desirable to accelerate and enhance rate control of the freezing process in order to avoid formation of intracellular ice crystals, to preserve the microscopic morphology of the tissue and to permit rapid examination of tumor surface margins in all types of tissue and sample sizes. This is accomplished in the apparatus of the present application by prechilling the tissue receiving plates and incorporating structure to distribute a thin layer of frost over the surface of the plates as well as structure to maintain the frost layer until the specimen is placed thereon.

SUMMARY OF THE INVENTION

The present invention is directed to improvements in an apparatus for freezing tissue specimens at cryogenic temperatures. Cryogenic operating temperatures present a number of problems that are overcome by the present invention and the present invention also provides for quicker freezing of the specimen to provide snap freezing as well as quicker warming of the apparatus after the freezing is complete, so as to quickly prepare the apparatus for subsequent specimens.

The apparatus includes a support structure upon which a pair of rotary motion platforms are pivotally mounted so as to rotate about parallel, but spaced, axes. The rotary motion platforms have open and non-covering positions wherein access is provided to an operator to prepare specimens on the surface of one of the rotary motion platforms while the opposite rotary motion platform is in a covering position covering a linear motion platform. The linear motion platform is spaced from and does not move with respect to the rotary motion platform until the rotary motion platform is in the covering position after which a trigger initiates movement of the linear motion platform in a vertical direction toward the rotary motion platform.

The apparatus includes a mechanism for automatically repositioning and locking the linear motion platform in a lowered position when one of the rotary motion platforms moves from the covering to the non-covering position. Likewise, the apparatus provides a mechanism for automatically triggering release of the linear motion platform to move toward a rotary motion platform when either one of the rotary motion platforms are placed in a covering relationship therewith.

The apparatus includes liquid nitrogen at cryogenic temperatures for cooling specimens in sets of opposed cryodiscs that align with one another in facing relationship on the linear motion and rotary motion platforms when in the covering position. The liquid nitrogen is conveyed to the rotary motion platforms through flexible plastic tubing which is preshaped into a coiled configuration that is very loosely wrapped about an axially positioned rod and which includes tails projecting in opposite directions. The tail associated with the movement of the rotary motion platform rotates 90° to either side of a preselected position and movement associated with this rotation is taken up by multiple separate loops within the coil, such that stress is spread along the coil. In this manner the tubing, which becomes fairly inflexible at cryogenic temperatures, is able to still provide sufficient flexure to handle movement of the rotary motion platform without breakage.

The cryogenic discs associated with the linear motion platform include central specimen receiving plates. The plates include a stem which extends axially through the cryogenic discs and that is engageable by a pylon attached to the base of the apparatus. The pylon engages the stem of the discs when the linear motion platform is lowered so as to raise the specimen receiving plate above the discs and maintain it in a relatively warm state prior to receiving the specimen when the rotary motion platform is placed above the linear motion platform. When the linear motion platform raises the stem, the stem disengages from the pylon and the specimen receiving platform lowers to be quickly cooled by the cryogenic discs.

Another embodiment of the apparatus includes a rapid frost system having a mechanism for depositing a layer of frost on the surface of the cryogenic discs associated with the linear motion platform. Comparatively cold nitrogen gas is employed to pressurize a water-filled nebulizer, which produces a fine and cold spray or mist of water. Exhaust from the vacuum pump conveys the spray through flexible plastic tubing to spray heads located on the linear motion platform. The spray heads evenly deliver a fine spray of water over the cryogenic discs. Liquid nitrogen is conveyed through flexible plastic tubing to the cryogenic discs associated with the linear motion platform in order to prechill them to about −10° C. to −20° C., so that the already cooled and nebulized water turns immediately to frost upon contact with the discs. The central specimen receiving plates contact the frost layer on the cryogenic discs, which provides better heat transfer from the specimen receiving plates and more rapid freezing of the specimen.

A system of heaters is provided to allow for quick heating of each of the cryogenic discs or only selected groups of the cryogenic discs. Preferably the heaters are triggered to start automatically when the linear motion platform lowers and includes a timer to heat for a preselected period. Heaters are also controlled by thermostats to prevent overheating.

The operator also has enhanced capability and flexibility with respect to being able to select freezing with respect to all of the cryodiscs associated with the linear motion platform or the alternative ability to select just certain groupings of those discs when there are only a small number of specimens to be frozen.

OBJECTS AND ADVANTAGES OF THE INVENTION

Therefore, the objects of the present invention are: to provide an apparatus for rapidly freezing tissue samples that is both user friendly and convenient to use; to provide such an apparatus that provides multiple preparation platforms that function in cooperation with a central platform and allow selective rotation of the preparation platforms over the central platform such that an operator may prepare samples on one of the platforms while the other has specimens undergoing freezing; to provide such an apparatus utilizing multiple rotary platforms that each trigger the central platform to move linearly with respect to the rotary platform once the rotary platform has stopped in place above the central linear motion platform; to provide such an apparatus wherein the platforms and especially cryodiscs located on the platforms are quickly prepared for subsequent specimens by heating the cryodiscs to non-cryogenic temperatures; to provide such an apparatus wherein specimen receiving discs in the linear motion platform are held in spaced relationship to the linear motion platform prior to engagement with the specimen, such that residual cooling from the linear motion platform does not prechill the specimen receiving disc and such that the specimen receiving disc and specimen are allowed to freeze generally simultaneously for better specimen control; to provide such an apparatus wherein flexible tubing is utilized to convey liquid nitrogen or other cryogenic fluids to discs on the rotary motion platforms; to provide such an apparatus wherein the flexible tubing is wrapped in comparatively large coils loosely about a central core such that upon movement of the rotary motion platform associated with the tubing, the rotary motion of the tubing is conveyed to the coils which allow restricted movement even at cryogenic temperatures such that the tubing is not broken during rotary movement at cryogenic temperatures; to provide such an apparatus including selection of cooling and heating for less than the total number of specimen receiving discs available such that an operator may utilize only certain of the discs if the number of specimens so require or all of the discs; to provide such an apparatus wherein heaters are thermostatically controlled to bring the specimen receiving cryodisc to a preselected temperature quickly without overheating; to provide such an apparatus having controls to allow a substantial amount of variance in cooling with all of available cryodiscs or with a smaller selected group of the cryodiscs so as to allow for better control and a wider variety of use of the apparatus; to provide a method of operation of the apparatus in accordance with the above objectives to allow an operator to have a wide range of control and ease of operation in utilizing the apparatus; to provide such an apparatus having a rapid frost system for depositing a layer of frost on the surface of the cryogenic discs associated with the linear motion platform; to provide such an apparatus wherein nitrogen gas is employed to pressurize a nebulizer and in conjunction with a vacuum pump is employed to spray nebulized water over the surface of cryogenic discs; to provide such an apparatus which permits rapid freezing of large tissue specimens having high fat content; to provide such an apparatus which is relatively easy to use, inexpensive to produce and especially well suited for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 12 is a general schematic flow diagram of a rapid frost system of the apparatus.

FIG. 13 is a side elevational view of a nebulizer of the rapid frost apparatus, with the right portion shown in cross section to show interior detail thereof.

FIG. 14 is a fragmentary cross sectional view of a cryodisc of the central linear motion platform, showing a layer of frost on the upper surface thereof, taken along line 10—10 of FIG. 3, with a tissue receiving plate positioned above the platform.

DETAILED DESCRIPTION OF THE INVENTION

I. Specimen Freezing Apparatus

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 6:
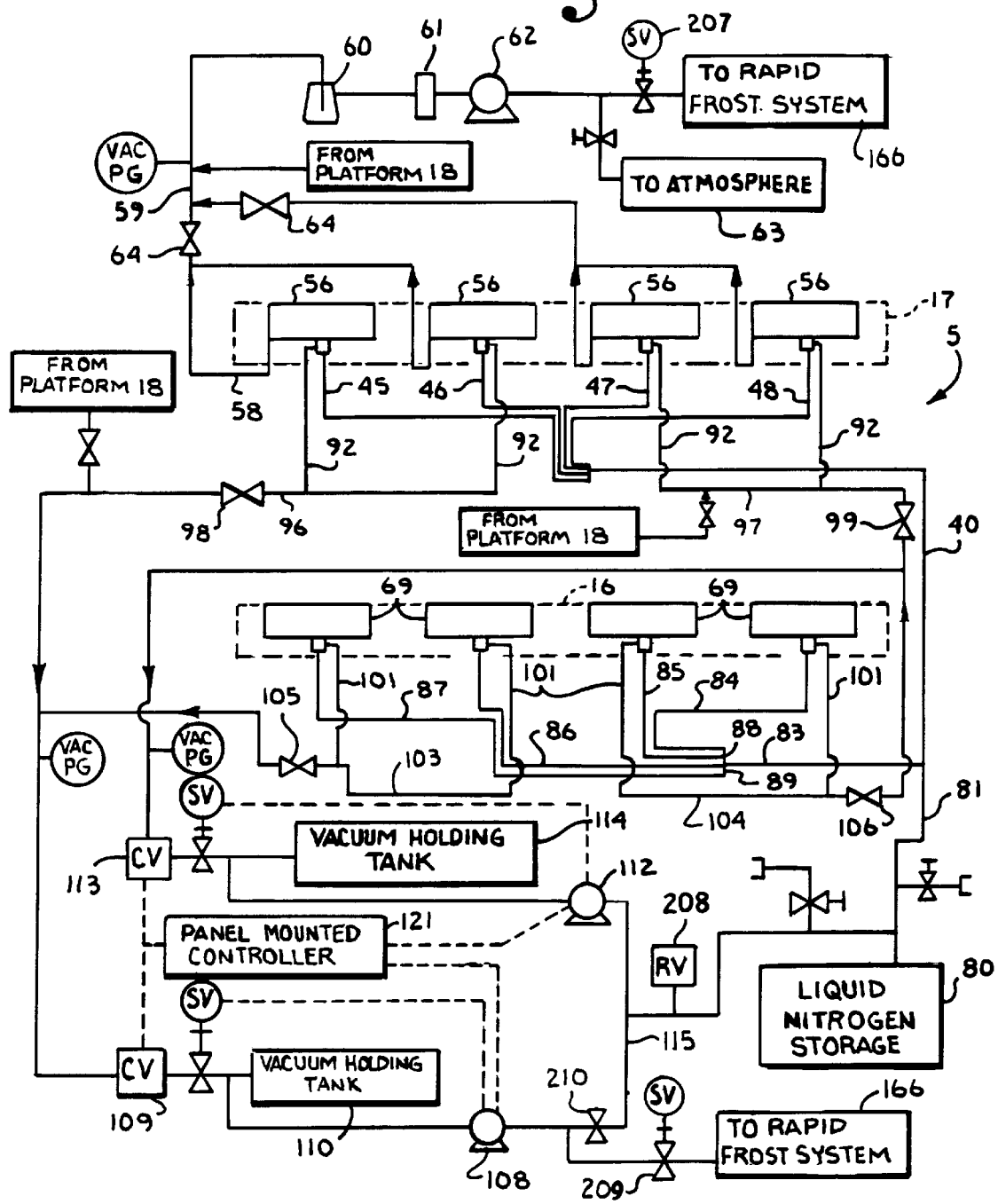
FIG. 6 is a general schematic flow diagram of a fluid flow system of the apparatus.

The reference numeral 1 generally represents a tissue specimen freezing apparatus in accordance with the present invention. The apparatus 1 includes a platform mechanism 3, a cabinet 4 and includes a fluid transfer system 5 which is schematically illustrated in FIG. 6.

The platform mechanism 3 includes a base 10 that is generally supported by the cabinet 4. Fixedly attached to and extending upwardly from both the front and rear ends of the base 10 are front and rear support panels 11 and 12. The support panels 11 and 12 support therebetween a pair of horizontally spaced columns 14 and 15 that are vertically spaced from the base 10, a single linear motion platform 16 and a pair of rotary or rotatable motion platforms 17 and 18.

The rotary motion platforms 17 and 18 selectively and initially receive specimens, such as specimen 19 which is placed on the apparatus 1 for the purpose of freezing the specimen 19.

The central column 14 and rotary motion platform 17 are essentially mirror images of the central column 15 and rotary motion platform 18. Consequently, where the description is directed specifically to one of these sets of columns and rotary motion platforms, the opposite is also seen to be described with a simple modification of making the opposite a mirror image. Each of the central support columns 14 and 15 are pivotally attached at opposite ends thereof to the support panels 11 and 12 so as to be rotatable about an axis thereof even at cryogenic temperatures.

Each of the support columns 14 and 15 also are joined to a respective rotary motion platform 17 and 18 and support a piping arrangement 20 which is operably part of and connected to the fluid transfer system 5. The piping arrangement 20 conveys a liquid cryogenic fluid, especially liquid nitrogen, to an associated rotary motion platform 17 or 18. The piping arrangement 20 also conveys away gaseous and potentially some liquid nitrogen from the rotary motion platforms 17 and 18. Although the present apparatus 1 is especially designed for use in conjunction with liquid nitrogen because it is generally inert and noncombustible, the apparatus 1 may also be used in conjunction with other cryogenic fluids. Because the central columns 14 and 15, the linear motion platform 16 and the rotary motion platform 17 and 18 and the piping arrangement 20 all must interact with and be able to withstand cryogenic temperatures which are often at least several hundred degrees below zero fahrenheit, each of these elements must be constructed to withstand such cold during normal and frequent use.

Figure 7:
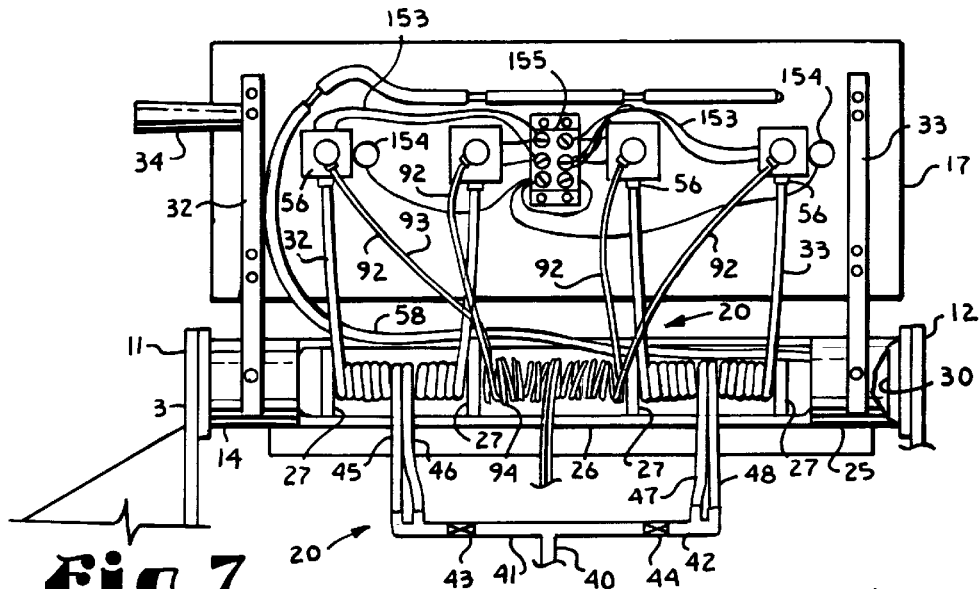
FIG. 7 is a fragmentary side elevational view of the apparatus with one of the rotary motion platforms positioned approximately halfway between the open position and the covering position thereof to show detail of the underside of the platform.

Directing attention to FIG. 7 and the central column 14, it is seen that the column 14 includes an elongate open tube 25 which is generally closed at ends thereof, but which includes a substantial central elongate section 26 which is semi-circular in shape. The central section 26, therefore, allows one half of the tube 25 to be fixedly open to receive the piping arrangement 20. Radially extending supports 27 are located along the interior of the tube 25 and are axially joined by a rod 29 that passes through the center of each of the supports 27. The opposite ends of each of the tubes 25 are sleeved on slidable circular insets 30 that are mounted on opposite support panels 11 and 12.

A pair of support arms 32 and 33 are fixedly attached to the tube 25 near opposite ends thereof and also to the rotary motion platform 17, such that rotation of either the support column 14 or the rotary motion platform 17 produces the same rotation in the opposite element. A handle 34 is attached to the support arm 32 to allow an operator to physically maneuver the rotary motion platform 17 and to rotate the support column 14.

The piping arrangement 20 includes a liquid nitrogen supply conduit 40 which is connected to a source of liquid nitrogen, as will be discussed in greater detail below. The supply conduit 40 diverges into first and second branches 41 and 42 which each include a control valve 43 and 44 respectively. The branch 41 further diverges into subbranches 45 and 46 and the branch 42 subdivides into subbranches 47 and 48.

Figure 5:
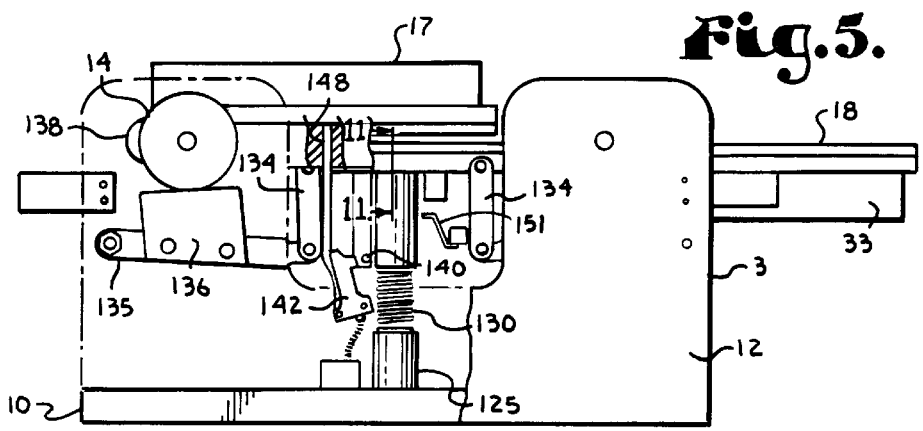
FIG. 5 is a rear elevational view of the apparatus with portions removed to show detail thereof and with the left rotary motion platform in a covering position and the central linear motion platform in a tissue engaging relationship subsequent to linear movement thereof.
Figure 8:
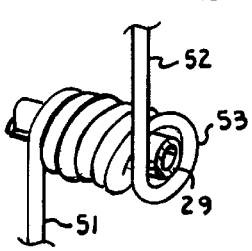
FIG. 8 is a fragmentary and perspective view of a portion of the cryogenic tubing of the apparatus.
Figure 9:
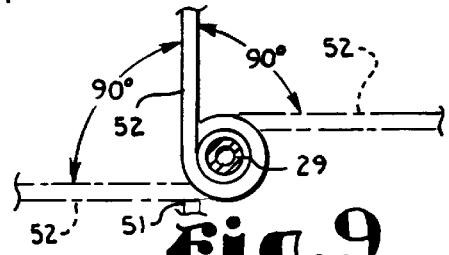
FIG. 9 is a rear elevational view of tubing of the apparatus shown in FIG. 8 showing movement between phantom lines illustrating a tail in different locations.

Each of the subbranches 45, 46, 47 and 48 are constructed of flexible tubing. A suitable tubing for this purpose has been found to be tetrafluoroethylene which is fourteen gauge having an internal diameter of 0.066 inches and a wall thickness of 0.008 inches. Each of the subbranches 45 through 48 include a pair of opposed tails 51 and 52 flow connected to a central coil 53. The coil 53 and tails 51 and 52 are initially heat set in the configuration shown in FIG. 8. The coil 53 is very loosely wrapped around the rod 29 so as to allow a significant amount of movement within each section or loop of the coil 53. Shown in FIG. 9 is movement of the tail 52 that is associated with the rotary motion platform 17 between the position where the rotary motion platform 17 is in an open configuration thereof as designated by the phantom lines in FIG. 9 and as seen in FIG. 5 to an upright position as seen by the central solid lines in FIG. 9 and as seen by the solid lines in FIG. 3 and thereafter movement to the covering position which is shown by the phantom lines to the left in FIG. 9. Through each of these movements the tail 52 rotates through an angle of approximately 90° which rotation is taken up by partial uncoiling or loosening of the coil 53 or is the opposite direction by tightening of the coil 53.

Because of the multiple loops within the coil 53, the movement of the tail 52 moves each of the loops only a comparatively small amount which does not exert a substantial amount of stress upon either the tails 51 or 52 nor the coil 53. In this manner the subbranches 45 through 48 are able to complete the rotation which allows the tail 52 to rotate from the upright position 90° to either side without fracturing because of rigidity caused by the cryogenic temperatures associated with the liquid nitrogen passing therethrough. During manufacture of each of the subbranches 45 through 48 the tails 51 and 52 are heat set to be in the position shown in FIG. 8. This allows for the least amount of stress to be placed on each of the subbranches 45 through 48 as the tail 52 rotates from the left position in FIG. 9 to the upright position or from the upright position to the right position.

Each of the rotary motion platforms 17 and 18 include four specimen receiving cryodiscs or simply discs 56. Surrounding each of the cryodiscs 56 is a groove 57 which is connected by ports in platform 17 to a conduit 58 that is seen in FIG. 6. Each of the conduits 58 join together in a common header 59 which passes through a liquid separation vessel 60, a protective filter 61 and through which gas is drawn by a vacuum pump 62 to discharge to the atmosphere as indicated by the block 63.

The grooves 57 in this manner allow a vacuum to be pulled by the vacuum pump 62 from the surface of each of the platforms 17 and 18 in the region surrounding the cryodiscs 56. Valves 64 separate the vacuum conduits 58 into branches that each serve two of the cryodiscs 56. A clear plastic sheet 66 is placed over a specimen, such as specimen 19 in FIG. 1, in such a manner as to extend radially outward from the groove 57. A vacuum grease is also placed on the platform 18 radially outward from the groove 57 and between the sheeting 66 and the surface of the platform 18. In this manner, when the vacuum pump 62 is operated and placed on line with the particular groove 57 associated with the disc 56 upon which the specimen 19 is placed, a vacuum is pulled through the groove 57 that draws the sheeting 66 tightly against the surface of the rotary motion platform 18, the disc 56 and the specimen 19 so as to compress the specimen 19 and to preferably draw any pockets of air from between the specimen 19 and the disc 56.

Figures 10, 11:
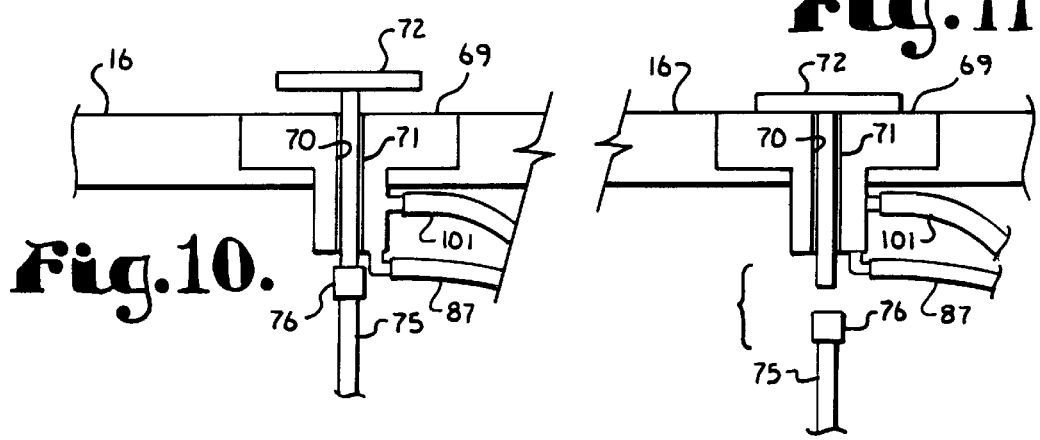
FIG. 10 is a fragmentary and cross sectional view of the linear motion platform, illustrating positioning of the platform prior to engagement with a specimen and with a specimen receiving plate in a raised position, taken along line 10—10 of FIG. 3.
FIG. 11 is a fragmentary cross sectional view of the linear motion platform, illustrating the tissue receiving plate in a lowered position relative to the platform and with the platform in a tissue receiving configuration, taken along line 11—11 of FIG. 5.

The linear motion platform 16 also has four discs 69 which are designed similar to but somewhat different from the disc 56. In particular, the discs 69 are similar to the discs 56 with the major exception of having a central hollow bore 70, as is seen in FIGS. 10 and 11. The bore 70 receives therein a stem 71 of a tissue receiving plate 72. During this freezing process, the specimen 19 is preferably first frozen on the rotary motion platform 18 and surrounded by embedding compound along with a retention ring. Thereafter, the rotary motion platform 18 is rotated about the central axis thereof to a covering position above the linear motion platform 16 and thereafter the linear motion platform 16 raises in a manner that will be discussed below. As the linear motion platform 16 raises the discs 69 face mating disc 56 and, in particular, an associated plate 72 engages either the specimen 19 directly or the embedding compound for the specimen 19 engages the plate 72 and freezes thereto. Later the specimen 19 will be removed from the platform 16 attached to the platform 72 that then functions as a carrier.

It has been found that it is preferable for the plate 72 to be approximately room temperature or at least warmer than cryogenic temperatures so that it will not be substantially colder as compared to the specimen 19 when the back side of the specimen 19 or the embedding compound is applied to the surface of the plate 72. The reason for this is that the specimen 19 and an embedding compound adhere better to the surface of the plate 72 when it is warmer such that it freezes together with the backside of the specimen 19.

During continuous operation of the apparatus 1, the linear motion platform 16 becomes inherently colder than the surrounding room temperature. Even when the discs 69 are warmed somewhat, the residual heat sink presented by the linear motion platform 16 may act to keep the plate 72 cold. Consequently, pylons 75 are mounted at spaced intervals along and upstanding from the base 10 at locations so as to be vertically aligned with each plate stem 71.

Each of the pylons 75 have an adjustable head 76 that is adapted to engage the lower end of the plate stem 71 when the linear motion platform 16 is lowered, such as is shown in FIG. 10. This in turn raises the plate 72 relative to the remainder of the linear motion platform 16 and disc 69 and this also places the plate 72 in spaced relationship thereto. This helps prevent the plate 72 from premature cooling. Once the linear motion platform 16 raises, such as is shown in FIG. 11 the stem 71 disengages from the pylon head 76 and the plate 72 lowers to the surface of the discs 69 so as to relatively very quickly cool when cryogenic fluid is applied to the disc 69. The discs 69 and 56 are structured to distribute liquid nitrogen in such a manner as to provide substantially quick cooling of the discs 56 and 69, especially the upper surface thereof in the manner more fully described in U.S. Pat. No. 5,628,197.

With reference to FIG. 6, liquid nitrogen is stored in a storage vessel 80. A supply conduit 81 receives liquid nitrogen from the storage vessel 80 and conveys nitrogen to the supply conduit 40 which in turn delivers it to the subbranches 45 through 48 that are in turn connected to discs 56 on rotary motion platforms 17 and 18. The conduit 81 also conveys liquid nitrogen to the supply conduit 83 which diverges into four subbranches 84 through 87 which supply liquid nitrogen to respective discs. Control valves at locations 88 and 89 separate the branches 84 and 85 into a single control group and the branches 86 and 87 into a single control group.

Gas return conduits 92 preferably convey only gas that has been evaporated because of heat transfer from the liquid nitrogen. Preferably the conduits 92 are constructed of one eighth inch inside diameter and three sixteenths inch outside diameter tetrafluoroethylene. The gas conduits 92 convey the gas away from the discs 56. Because the gas conduits 92 also can become quite brittle due to low temperatures, the conduits 92 also incorporate tails 93 and coils 94 that are loosely coiled about the rod 29. The gas conduits 92 are joined in pairs by headers 96 and 97 through which flow is controlled by valves 98 and 99. Gas conduits 101 join with the discs 69 and receives gas flow therefrom. Pairs of the conduits 101 are joined into headers 103 and 104 through which flow is controlled by valves 105 and 106. The headers 96 and 103 are joined together and gas directed into a vacuum pump 108 through a control valve 109 and is also joined with a vacuum holding tank 110. Headers 97 and 104 are also joined and gas flow is directed into and through a vacuum pump 112 as well as through a control valve 113 and in association with a vacuum holding tank 114. Both of the vacuum pumps 108 and 112 discharge into a conduit 115 that returns to the liquid nitrogen storage tank 80. A control panel 120 includes a power controller 121 and control switches 122 and 123 for operating the pumps 108 and 112 respectively. Also on the control panel 120 are switches 156 and 157 that link to valves 43, 44, 64, 88, 89, 98, 99, 105, 106, 109 and 113 so as to allow an operator to control liquid nitrogen flow to either rotary motion platform 17 or 18 (switch 156) and to select only the front two pairs of sets of discs 56 and 69 or operation of all discs associated with use of one of the rotary motion platforms 17 and 18 simultaneously.

Turning attention to the linear motion platform 16, it is noted that there is a control mechanism 124 for controlling the timing and the motion of the platform 16. This mechanism is shown in FIGS. 2 through 5 in some detail and attention is directed to those figures.

In particular, when dealing with specimens of the type frozen by the apparatus 1 of the present invention, it is desirable that the specimens 19 not be rolled with respect to the surface, but rather maintained flat, so it is best to not disengage the important entire lower and marginal surfaces of the specimen 19 from the upper surface of the discs 56 until removal from the apparatus 1. Because the rotary motion platforms 17 and 18 have rotary motion, it would be possible to exert sideways movement on the specimen 19 if these platforms 17 and 18 are allowed to engage the linear motion platform 16 while still in rotary motion. Consequently, the present invention is designed to allow the rotary motion platforms 17 and 18 to complete the rotary motion thereof prior to any movement by the linear motion platform 16 and before the linear motion platform 16 engages the specimen 19. All movement of the linear motion platform 16 is linear or in a straight line so as to be less likely to roll the specimen 19.

The linear motion platform 16 is supported by a pair of legs 125. Each of the legs 125 includes an upper segment 127, a lower segment 128 that is mounted on the base 10, a slidable central rod 129 and a biasing spring 130. In this manner the rod 129 allows linear relative vertical motion between the upper segment 127 and the lower segment 128 while the platform 16 is continuously biased upwardly by the spring 130. Thus the linear motion platform 16 is always urged upwardly against constraints, as described below.

Figure 3:
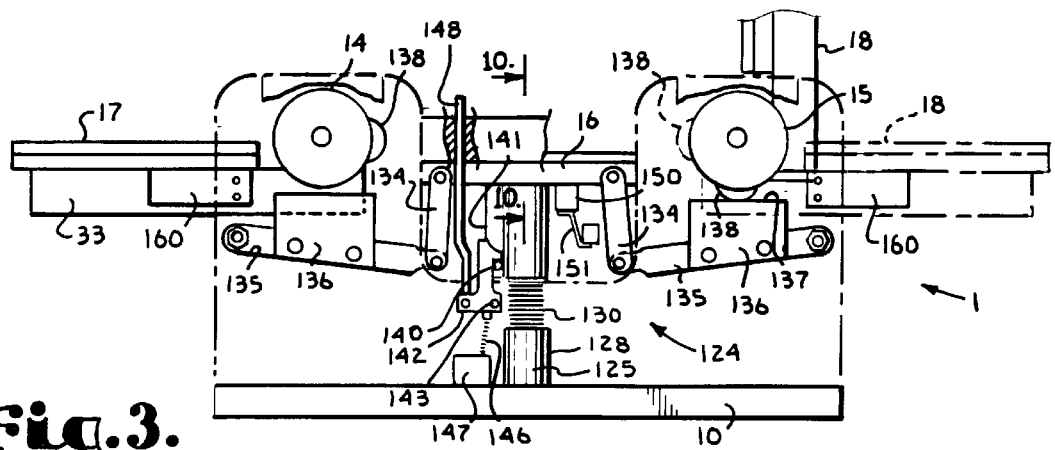
FIG. 3 is a rear elevational view of the apparatus with portions broken away to illustrate detail of the apparatus and with one of the tissue receiving plates shown in an open position thereof and the opposite shown in a partially open position with an open position of the opposite rotary motion platform shown in phantom lines.
Figure 4:
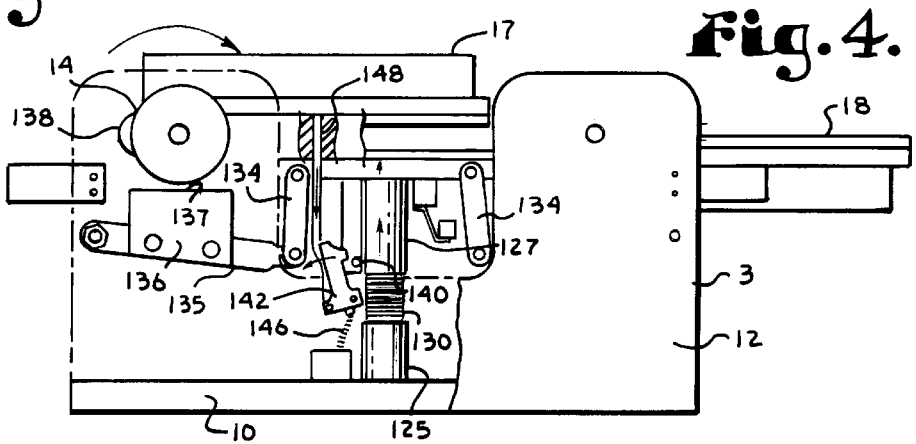
FIG. 4 is a rear elevational view of the apparatus with portions removed to show detail thereof with the left rotary motion platform just having been swung to a covering position thereof and just at the point of release of a linear movement platform.

With reference to FIGS. 3 through 5, the linear motion platform 16 is also linked on each side by pairs of links 134 and 135 to the support panels 11 and 12. The links 134 are generally vertical and are vertically aligned, whereas the links 135 are slightly angled, but generally horizontally aligned. Each of the links 135 include a cam follower 136 with an upper surface 137.

Projecting outward from each of the rotary motion platform central columns 14 and 15 are cam followers 136. As seen in FIG. 3, as the cam follower 136 rotates with the central shaft 15 the cam 138 rotates into engagement with the surface 137 of the cam follower 136 and urges the cam follower 136 with the attached links 135 and 134 downwardly. This in turn urges the linear motion platform 16 downwardly against the spring 130.

Figure 1:
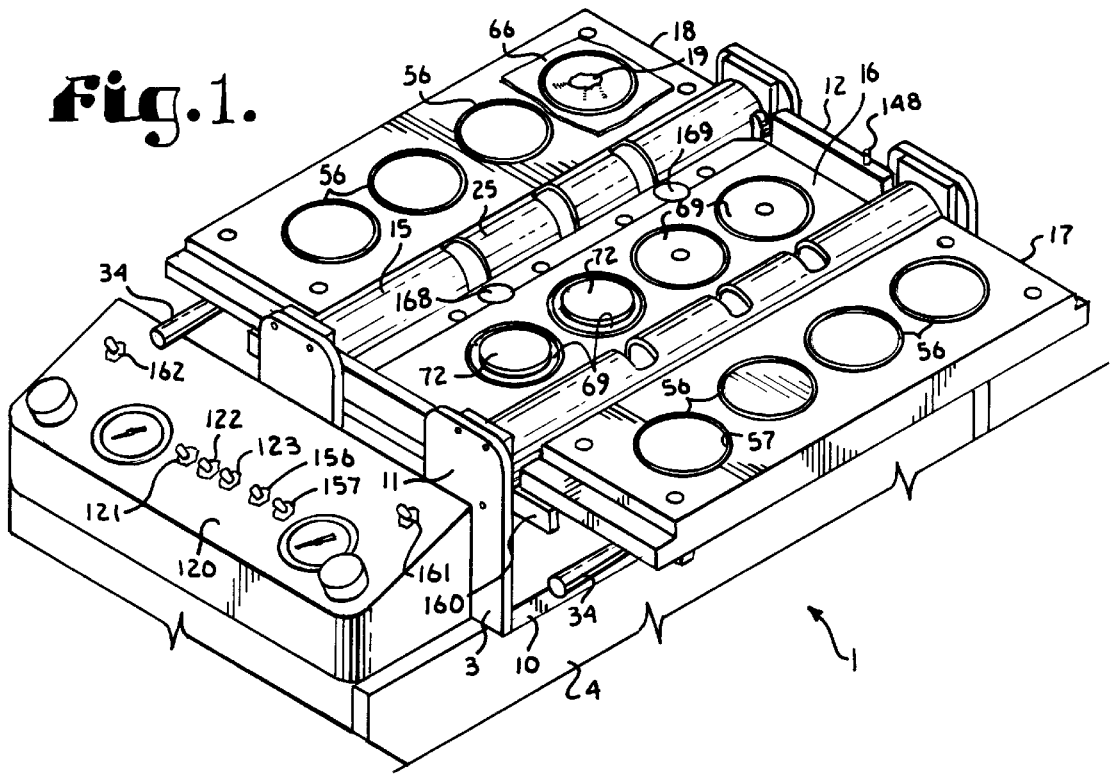
FIG. 1 is a fragmentary perspective view of a tissue freezing apparatus in accordance with the present invention, including a support cabinet for enclosing a liquid nitrogen system and illustrating the apparatus with both tissue receiving rotary motion platforms in an open and tissue receiving configuration thereof.
Figure 2:
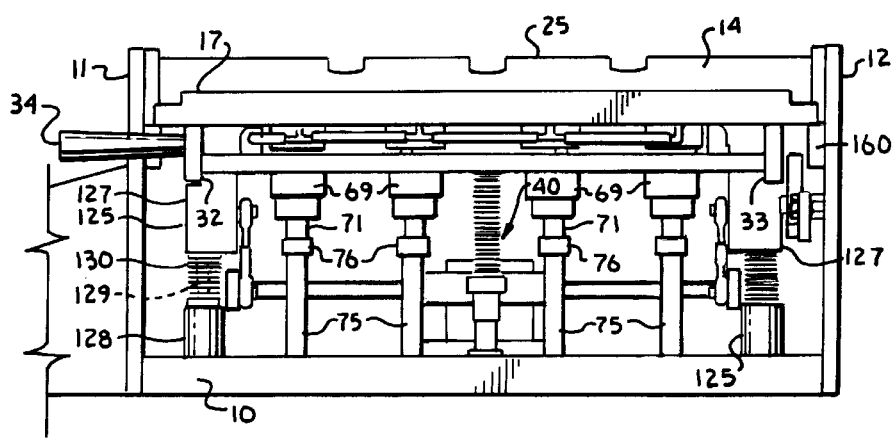
FIG. 2 is a fragmentary side elevational view of the apparatus.

A latch peg 140 extends outwardly from a strut 141 attached to and depending downwardly from the linear motion platform 16. A latch 142 is pivotally attached by a pivot pin 143 to the support panel 12. As the pin 140 descends the latch 142 automatically engages and secures the pin 140 preventing the linear motion platform 16 from rising. A spring 146 attached to the base 10 by a block 147 urges the latch 142 to maintain the linear motion platform 16 in the lowered position against the spring 130. A release rod 148 is attached to the latch 142 opposite the pin 140 and extends upwardly through the support panel 12 as is shown in FIGS. 1 and 3. When one or the other of the rotary motion platforms 17 or 18 is positioned above the linear motion platform 16 and engages the rod 148 it depresses the rod and releases the pin 140 from the latch 142 so as to allow the linear motion platform 16 to raise under urging of the spring 130. In this manner the linear motion platform 16 does not move until the rotary motion platforms either 17 or 18 have completed their rotary motion and are located above the linear motion platform 16. A bar 149 connects and coordinates the mechanism 124 at both front and rear of the apparatus 1.

Depending from the linear motion platform 16 is a trigger block 150 which engages a trigger 151 when the linear motion platform 16 is lowered. The trigger 151 initiates electrical current through a heater circuit having elements 153, as seen in FIG. 7. The heater elements 153 are resistance heaters which encircle and/or engage the discs 56 and 69 and heat the discs 56 and 69 in preparation for subsequent specimen handling. The heating elements 153 are also connected to thermostats 154 on every other disc 56 or 69 which effectively segregates the discs and allows heating of those discs to a predetermined temperature as determined by the thermostats 154. In this manner the discs 56 and 69 are not overheated and the heating can be controlled by grouping. The heater circuit also includes a timer located at panel 155 to allow automatic timing of the heating. Normally, heating requires about three minutes. Freezing normally requires about 30 to 45 seconds with the rotary motion platform 17 or 18 in the open position and another 30 to 45 seconds in the covering position; however times vary with the specimen being treated.

A complete sequence of operation of the rotary motion platform 16 and 17 can be seen in FIGS. 3 through 5. In particular, FIG. 3 shows the right hand rotary motion platform 18 being returned from a covering position to an open position and placed on a stop 160 (phantom lines). The solid lines show it located in approximately the half way position with the cam 138 engaging the surface 137. That is during movement from the covering position to the open position, the cam 138 engages the surface 137 of the cam follower 136 and urges the linear motion platform 16 downwardly into a locked position held in the locked position by the latch 142 engaging the latch pin 140.

Subsequently, the left hand rotary motion platform 17 is moved from a fully open position as seen in FIG. 3 to a covering position as seen in FIG. 4, but prior to movement of the linear motion platform 16. In particular, the linear motion platform 16 engages the rod 148 and pushes the rod 148 downwardly so as to rotate the latch 142 out of engagement with the pin 140 thereby releasing the linear motion platform to rise and disengaging the block 150 from the switch 151.

FIG. 5 shows the linear motion platform 16 in the raised position. It is noted that operation to rotate either one of the rotary motion platforms 17 or 18 from the open position to the covering position triggers the rod 148 and thus initiates movement of the linear motion platform 16. Likewise, movement of either of the rotary motion platforms 17 or 18 from the covering position, such as is shown by the platform 17 in FIG. 5, to the open position, such as is shown in FIG. 3, resets the linear motion platform 16 in the lowered position so that it is automatically ready for use with a different or even the same rotary motion platform 17 or 18 at a later time.

Much of the use of the present invention has been described in the above description. In general, the present invention provides certain distinct advantages over the prior art in that either of a pair of rotary motion platforms 17 or 18 can be selectively utilized for preparation of samples while the other is being used to freeze samples which effectively substantially speeds up operation of the process when multiple specimens are to be analyzed. The twin rotary motion platforms 17 and 18 are designed to cleverly utilize the triggering mechanism which includes the release rod 148 to unlock the linear motion platform 16 and to automatically allow it to move toward the rotary motion platforms 17 or 18 once the rotary motion has ceased. The apparatus 1 also provides for automatic resetting of the linear motion platform 16 by simply moving the rotary motion platform 17 or 18 from the covering position to the open position thereof.

During use of the invention, the cryogenic supply tubing of the piping arrangement 20 allows the coils 53 associated with the liquid nitrogen supply and the coils 94 associated with the return gas conduits 92 for drawing away the evaporated gas from the discs 56 and 69 to allow substantial improvement over the prior art since the coils 53 and 94 are constructed of fairly inexpensive and relatively easy to obtain flexible plastic tubing as compared to more exotic and expensive structures. This is accomplished by having a substantial number of loops in the coils 53 and 94 that are loosely coiled about a central rod 29 and which allow at least 90° movement of the tail 52 or 93 of the tube in either direction due to spreading the forces of expansion over a substantial number of individual loops within the overall coils 52 or 93.

The present invention likewise provides a great deal more flexibility to the operator in that the operator can elect to operate only two of the specimen receiving discs 56 on only one platform 17 or 18 by use of selector switches 157 without having to apply liquid nitrogen to and withdraw gaseous liquid nitrogen from the remaining discs 56. This allows the operator to handle as many as two or a great number of specimens within a relatively short period of time. Switches 161 and 162 also allow the operator to initiate either manual or timed freezing on like sides of the apparatus 1. The heater elements 153 provided with the present invention heat the discs 56 and 69 at the conclusion of the freezing operation so as to ready the discs 56 and 69 for subsequent specimen freezing. The heater elements 153 are designed to work also in conjunction with less than a total number of discs 56 and include thermostats to prevent overheating.

II. Rapid Frost System

In accordance with the present invention a rapid frost system 166 is utilized in conjunction with the previously described tissue freezing apparatus 1. The rapid frost system 166 includes a nebulizer 167, spray heads 168, 169, 170, 171 and a nebulized fluid transfer system 172, which is schematically illustrated in FIG. 12.

As shown in FIG. 13, the nebulizer 167 is of conventional construction and includes a generally elliptical lower housing member 176 surmounted by a stepped upper housing member 177, each provided with mating detent structures 178, 179 for locking engagement when the housing members are rotated relative to each other.

Lower housing member 176 includes continuous walls 180, circumscribing a reservoir 181 adapted to be filled with water. An axially oriented tubular pipe 185 having a constricted opening uppermost end 186 is integrally joined with the lower housing 176. Pipe 185 extends from a position well within the reservoir 181 and downwardly out through the lowermost portion thereof for intercoupling with the nebulized fluid transfer system 172. Lower housing 176 is supported on cabinet 4 by downwardly projecting spaced legs 187.

A spray assembly 188 includes a tubular portion 189 which is coaxially mounted over the reservoir portion of pipe 185. The tubular portion 189 presents a generally cup-shaped constricted open upper end 190. A generally basket-shaped coupling 191 extends upwardly from the tube portion 189.

The upper nebulizer housing 177 includes stepped sidewalls 195 and a top 196. An axially oriented tubular pipe 197 is integrally joined with the top 196. Pipe 197 extends from a position well within the reservoir upper housing 177 and upwardly out through the top 196 for intercoupling with the nebulized fluid transfer system 172. The lowermost portion of pipe 197 terminates in a series of depending spaced legs 198 from which depends an annular deflector 199 having a central boss 200. Those skilled in the art will note that a pressure nebulizer is shown and described. However, so-called mechanical, electronic, heat or other type of conventional nebulizers or any other device capable of nebulizing water into small droplets may be employed. More than one nebulizer may also be employed.

The nebulized fluid transfer system 172 includes tissue vacuum exhaust conduit 205, which is flow connected to pump 62 and liquid nitrogen conduit 206, which is connected to pump 108. Conduit 205 includes a solenoid control valve 207. Conduit 206 includes a relief valve 208 and a solenoid valve 209. A ball check valve 210 (FIG. 6) prevents backflow of liquid nitrogen from storage 80 to the nitrogen vacuum reservoir. Conduit 206 supplies nitrogen gas to the pressurize nebulizer 167. A nebulized water and air stream is carried by conduit 211, which joins with conduit 205 in a common manifold 212. The conduit then diverges into branches 213 and 214. The branches 213 and 214 further diverge into subbranches 215, 216, 217 and 218, which in turn are coupled to respective spray heads 168, 169, 170 and 171, which open onto the linear motion platform 16.

In the rapid frost system 166, the cryodiscs 69 are prechilled to about −10° C. to −20°. The cryodiscs 69 are then coated with a thin layer of frost 221 by the frost system 166 by distribution of the gas stream carried to and through the spray heads 168, 169, 170 and 171. The tissue receiving plates 72 are installed on the cryodiscs 69 after the rapid frost cycle has been activated. Advantageously, the frost layer 221 functions to accelerate heat transfer from the tissue receiving plates 72 to the discs 69 and to provide more predictable, rate-controlled freezing.

In use, nebulizer reservoir 181 is manually filled with a supply of about 15 to 20 milliliters of water. Distilled water is preferred to avoid contamination of the apparatus with salt deposits. Control valve 209 opens, permitting conduit 206 to convey nitrogen gas that has been used to cool cryodiscs 56 and 69 to the nebulizer pipe 185. The nitrogen gas pressurizes the nebulizer 167 by passing through the constricted open pipe upper end 186, through the constricted open tube upper end 190. The pressurized nitrogen is deflected off boss 200 and passes through the liquid water in reservoir 181 causing a portion of the water to be entrained in an aerosol mist. Conduit 211 conveys the nebulized water-nitrogen gas mixture from nebulizer pipe 197 to manifold 212. Once the nebulizer 167 is pressurized, the solenoid control valve 207 is opened, permitting conduit 205 to deliver tissue vacuum exhaust containing air and some moisture to the manifold 212 to boost the rate of air flow across the cryodiscs 69. Solenoid control valves at locations 207 and 209 are operated by associated automatic controllers.

The mixture of nebulized water, nitrogen gas and air is conveyed through branches 213 and 214 to subbranches 215, 216, 217, and 218 and out through spray heads 168, 169, 170 and 171. As best shown in FIG. 14, the mixture flows across discs 69, where the reduced temperature of the prechilled discs 69 causes the nebulized water vapor to precipitate as frost 221. Thereafter, the frost coating 221 can be maintained by keeping the temperature of the discs 69 below about 0° C.

The nebulizer 167 is generally pressurized and permitted to run for about 60 seconds to about 120 seconds, until a thin coating of frost 221 appears on discs 69. A tissue receiving plate 72 is then mounted atop a disc 69 by inserting stem 71 into bore 70 and rotary motion platform 17 or 18 is actuated to the covering position. The frost coating 221 enhances heat transfer so that the specimen 19 consistently freezes more quickly and with superior microscopic morphology.

The present invention provides high quality snap frozen specimens in a comparatively very fast time. A fairly large tissue sample that is divided into eight sections for study can be quick frozen in about five minutes with very good quality. While the present invention is normally used to produce frozen specimens, it is foreseen that it may also be utilized to make permanent sections for microscopic study. In particular a solution of ten percent formaldehyde is applied to the frozen specimen which is then allowed to thaw. The specimen is "fixed" in planar configuration for use as a permanent section.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for quick freezing a tissue specimen comprising:
   a) a frame;
   b) a linear motion platform having thereon at least one surface adapted to engage a tissue specimen; said linear motion platform mounted on said frame and being moveable only along a generally linear path;
   c) first and second rotary motion platforms each having a tissue engaging surface; said first and second rotary motion platforms being mounted on said frame so as to be rotatable about a pair of respective spaced axes; said first and second rotary motion platforms each having a non-covering position wherein each rotary motion platform is adapted to receive a specimen and a covering position wherein a respective tissue engaging surface of each of said rotary motion platforms is in facing relationship to said linear motion platform surface; said first and second rotary platforms being configured such that only one thereof may be positioned in said covering position at any one time;
   d) a locking mechanism operably preventing said linear motion platform from moving toward either of said first and second rotary platforms unless one of said first and second platforms is fully in the covering position thereof;
   e) a cryogenic cooling system operably flow connected to said first and second rotary platforms and said linear motion platform to provide cryogenic cooling thereto; and
   f) a rapid frost system operably flow connected to said linear motion platform to provide a frost layer thereon.

2. The apparatus according to claim 1 wherein:
   a) each of said platforms includes at least one cryogenic disc having a surface for positioning on opposed sides of a specimen when one of said first and second rotary motion platforms is in the covering position thereof;
   b) said cryogenic discs are connected by a piping arrangement to a source of cryogenic fluid for operably chilling said discs; and
   c) said rapid frost system includes a nebulizer operably converting water to moisture vapor; said cryogenic cooling system is operably flow connected to said nebulizer to convey moisture vapor from said nebulizer to said cryogenic disc surface associated with said linear motion platform for operably producing a layer of frost on said cryogenic disc surface associated with said linear motion platform.

3. The apparatus according to claim 2 wherein said rapid frost system includes:
   a) a nitrogen entrained nebulizer for converting liquid water into an aerosol mist;
   c) a spray head for delivering said aerosol mist to said cryogenic disc surface associated with said linear motion platform; and
   c) a conduit flow intercoupling said nebulizer and said spray head.

4. The apparatus according to claim 3 wherein:
   a) said rapid frost system further includes a pump operably coupled with said nebulizer.

5. The apparatus according to claim 1 wherein:
   a) said linear motion platform includes at least one cryodisc located thereon;
   b) said cryodisc having an upper surface and an axial bore therethrough;
   c) a fluid nebulizer system being operably flow coupled with said cryodisc for distributing a cooled water aerosol to the surface of said cryodisc when said cryodisc has been chilled by the cryogenic cooling system to form a frost layer thereon; and
   d) a tissue receiving plate including a stem for receiving in and extending through said cryodisc bore permitting said plate to rest on said frost layer for accelerating heat transfer from said plate to said disc.

6. The apparatus according to claim 2 including:
   a) a switch to automatically initiate nebulization of the water by said nebulizer when said cryogenic cooling system is actuated.

7. The apparatus according to claim 6 including:
   a) a timer to limit operation of said nebulizer.

8. The apparatus according to claim 1 including:
   a) a fluid conduit receiving cold nitrogen from said platforms and conducting said cold nitrogen to said rapid frost system.

9. The apparatus according to claim 8 wherein:
   a) said fluid conduit is a first fluid conduit conducting said cold nitrogen to a water nebulizer so as to form an aerosol of water with the cold nitrogen; and including:
   b) a second conduit flow connected with said first conduit downstream of said nebulizer and conveying air into said first conduit.

10. In a cryogenic freezing apparatus wherein a cryogenic cooling system provides cryogenic cooling to a disc having a generally planar surface; the improvement comprising:
    a) a nebulizer operably flow coupled with said planar disc surface for producing an aerosol containing water and flow conduit for distributing said aerosol on said cooled surface to form a layer of frost thereon; said disc surface being sized and shaped to receive a tissue specimen subsequent to said layer of frost being formed thereon.

11. The apparatus according to claim 10 wherein:
    a) a cryogenic gas provides the cryogenic cooling to said disc and said conduit thereafter conveys said gas to said nebulizer to form said aerosol.

12. In an apparatus for freezing tissue specimens having a tissue receiving platform that moves for receiving a specimen, the improvement comprising:
    a) said platform having at least one cryodisc thereon adapted to be chilled by cryogenic fluid; said cryodisc including a generally planar upper surface;

b) a fluid nebulizer being operably flow coupled with said cryodisc for distributing nebulized fluid to the surface of said cryodisc when said cryodisc has been chilled by the cryogenic fluid so as to form a frost layer thereon; said planar upper surface being sized and shaped to receive a specimen thereon subsequent to said frost layer being formed thereon; and c) a specimen engaging plate including a stem sized and shaped to be received in and extend through said cryodisc permitting said plate to rest on said frost layer when said plate engages said platform.

13. The apparatus according to claim 12 including:

a) a cryogenic fluid source;

b) said source being flow connected with said platform and with said nebulizer to supply cool fluid thereto; and c) said nebulizer being flow connected to spray heads to deliver an aerosol of water and said fluid to said platform surface to produce said frost layer.

* * * * *